United States Patent
Maverick et al.

(10) Patent No.: US 9,902,743 B2
(45) Date of Patent: Feb. 27, 2018

(54) COPPER COMPLEX FOR CAPTURING CARBON DIOXIDE

(71) Applicants: Andrew W. Maverick, Baton Rouge, LA (US); Uttam R. Pokharel, Baton Rouge, LA (US); Frank R. Fronczek, Baton Rouge, LA (US)

(72) Inventors: Andrew W. Maverick, Baton Rouge, LA (US); Uttam R. Pokharel, Baton Rouge, LA (US); Frank R. Fronczek, Baton Rouge, LA (US)

( * ) Notice: Subject to any disclaimer, the term of this patent is extended or adjusted under 35 U.S.C. 154(b) by 0 days.

(21) Appl. No.: 15/029,147

(22) PCT Filed: Oct. 13, 2014

(86) PCT No.: PCT/US2014/060249
§ 371 (c)(1),
(2) Date: Apr. 13, 2016

(87) PCT Pub. No.: WO2015/057559
PCT Pub. Date: Apr. 23, 2015

(65) Prior Publication Data
US 2016/0257702 A1  Sep. 8, 2016

Related U.S. Application Data

(60) Provisional application No. 61/890,403, filed on Oct. 14, 2013.

(51) Int. Cl.
C07F 15/00 (2006.01)
C07F 1/08 (2006.01)
C07C 51/02 (2006.01)
C07C 51/41 (2006.01)

(52) U.S. Cl.
CPC ............. C07F 1/08 (2013.01); C07C 51/02 (2013.01); C07C 51/418 (2013.01)

(58) Field of Classification Search
None
See application file for complete search history.

(56) References Cited

U.S. PATENT DOCUMENTS

2008/0217606 A1  9/2008  Cheng et al. ............... 257/40

FOREIGN PATENT DOCUMENTS

CN  103265567  8/2013

OTHER PUBLICATIONS

Bünzli-Trepp, U. Systematic Nomenclature of Organic, Organometallic and Coordination Chemistry 1st Ed. EPFL Press-CRC Press. 2007, p. 2.*
Crowley, JD. et al. A multicomponent CuAAC "click" approach to a library of hybrid polydentate 2-pyridyl-1,2,3-triazole ligands: new building blocks for the generation of metallosupramolecular architectures. Dalton Transactions. 2010, vol. 39, p. 617.*
Bouwman, E. et al. Electrocatalytic CO2 Conversion to Oxalate by a Copper Complex. Dalton Transactions. 2010, vol. 327, p. 313.*
Cowan, JA. et al. Inorganic Biochemistry. Wiley. 1997, p. 6.*
Angamuthu, R. et al., "Electrocatalytic $CO_2$ Conversion to Oxalate by a Copper Complex," Science, vol. 327, pp. 313-315 (2010).
Horn et al. , "Nickel(I)-mediated transformations of carbon dioxide in closed synthetic cycles: reductive cleavage and coupling of CO2 generating NiICO, NiIICO3 and NiIIC2O4NiII) entities," Chem. Commun. 49, 10923-10925 (2013).
Pokharel et al., "Copper Complex for Fixing Carbon Dioxide to Oxalate and Carbonate," Mardi Gras Symposium 2014 Poster Presentation 27 (2014).
Vellas et al., "[Fe2L3]4+ Cylinders Derived from Bis(bidentate) 2-Pyridyl-1,2,3-triazole 'Click' Ligands: Synthesis, Structures and Exploration of Biological Activity," Molecules, vol. 18, pp. 6383-6407 (2013).

* cited by examiner

*Primary Examiner* — Andrew D Kosar
*Assistant Examiner* — Ben S Michelson
(74) *Attorney, Agent, or Firm* — John H. Runnels (57) ABSTRACT

A composition and method are disclosed for capturing $CO_2$. A pollutant/greenhouse gas can be converted into a valuable organic compound using a nontoxic reducing agent. $CO_2$ may be economically captured from the atmosphere, from products of combustion, or from byproducts of various chemical processes. The method reduces $CO_2$ in a three-step reaction cycle, in which a binuclear metal-organic compound converts $CO_2$ to oxalate in a redox cycle under mild conditions.

8 Claims, 9 Drawing Sheets

COPPER COMPLEX FOR CAPTURING CARBON DIOXIDE

This is the United States national stage of international application PCT/US2014/060249, international filing date Oct. 13, 2014, which claims the benefit of the Oct. 14, 2013 filing date of U.S. provisional patent application Ser. No. 61/890,403 is claimed under 35 U.S.C. § 119(e). The complete disclosure of the priority application is hereby incorporated by reference in its entirety.

This invention was made with Government support under Louisiana EPSCoR award number EPS-1003897 awarded by the National Science Foundation. The United States Government has certain rights in the invention.

TECHNICAL FIELD

This invention pertains to a composition and method for reducing carbon dioxide to oxalate.

BACKGROUND ART

An economical route for converting carbon dioxide to value-added organic compounds would be highly desirable because of the role carbon dioxide ($CO_2$) plays in global climate change, and in the depletion of fossil fuel resources. Although $CO_2$ is an inexpensive, non-toxic, abundant carbon feedstock, it is difficult to economically reduce $CO_2$ to a more useful form because of its thermodynamic stability and kinetic inertness. For $CO_2$ reduction to be attractive on a large scale, the process needs to work under mild reaction conditions, and the process must be economical.

$CO_2$ has traditionally been captured by absorption into a solution of an organic amine. This method is energy-intensive; it requires heating the solution to disperse the absorbed $CO_2$ for storage. If the absorbed $CO_2$ is simply driven off, then it must be stored somewhere (e.g. in an underground rock formation) to avoid release into the atmosphere.

Other methods that have been tried include activating and reducing $CO_2$ by electrochemical and electrocatalytic means in the presence of various transition metals and alloys.

There have been reports of using low-valent d-block and f-block metal complexes to reduce $CO_2$ to oxalate. Horn, B., Limberg, C., Herwig, C. & Braun, B. Nickel(I)-mediated transformations of carbon dioxide in closed synthetic cycles: reductive cleavage and coupling of $CO_2$ generating $Ni^{I}CO$, $Ni^{II}CO_3$ and $Ni^{II}C_2O_4Ni^{II}$) entities. *Chem. Commun.* 49, 10923-10925, doi:10.1039/C3cc45407j (2013) reported the use of β-diketiminate-based nickel(I) complexes to reduce $CO_2$ to CO or $C_2O_4^{2-}$ in two closed synthetic cycles. A significant limitation of the Horn et al. system was its use of $KC_8$, one of the strongest reducing agents available, to reduce Ni(II) to Ni(I).

Angamuthu, R., Byers, P., Lutz, M., Spek, A. L. & Bouwman, E. Electrocatalytic $CO_2$ Conversion to Oxalate by a Copper Complex. *Science* 327, 313-315, doi:10.1126/science.1177981 (2010) reported a binuclear copper(I) complex that can reduce $CO_2$ to oxalate, forming a tetranuclear copper(II) oxalate complex. Oxalate was then released by electrolysis, using lithium perchlorate as the supporting electrolyte, to complete the electrocatalytic cycle. The complex contained an amino-acid-derived ligand that bound two Cu atoms. Two of the complexes reacted with four $CO_2$ molecules to form two oxalates: $2Cu_2L+4CO_2 \rightarrow Cu_4L_2(C_2O_4)_2$.

Crowley, J. D.; Bandeen, P. H., A multicomponent CuAAC "click" approach to a library of hybrid polydentate 2-pyridyl-1,2,3-triazole ligands: new building blocks for the generation of metallosupramolecular architectures. *Dalton Trans.* 2010, 39, 612-623; doi: 10.1039/B911276F discloses a CuAAC reaction for generating alkyl, benzyl or aryl linked polydentate pyridyl-1,2,3-triazole ligands from the corresponding halides, sodium azide, and alkynes. Complexes with Ag(I) were described.

Other methods to reduce $CO_2$ include electrochemical or photochemical processes. In the Bocarsly "liquid light" approach, $CO_2$ reacts with an electrochemically-reduced solution of a heterocyclic amine such as pyridine. In photochemical reduction, some or all of the energy needed for $CO_2$ reduction is supplied by light.

Reductive dimerization of carbon dioxide to oxalate ($C_2O_4^{2-}$) converts an environmental pollutant into a more useful organic compound. There is an unfilled need for improved, economical methods to reduce $CO_2$ to oxalate. If a suitable chemistry could operate rapidly and cleanly enough, then it could be used to capture $CO_2$ from the atmosphere or from other chemical processes (e.g. combustion, cement manufacture). Oxalate and oxalic acid have many uses, including in extractive metallurgy, as mordants in dyeing processes, as bleaching agents, as miticides, and as reagents in various synthetic processes. In very large quantities, oxalate may also simply be used to sequester $CO_2$ in solid form, e.g. as $CaC_2O_4$.

DISCLOSURE OF THE INVENTION

We have discovered a novel composition and method for capturing $CO_2$. A pollutant/greenhouse gas can be converted into a valuable organic compound using a nontoxic reducing agent. $CO_2$ may be economically captured from the atmosphere, from products of combustion, or from byproducts of various chemical processes.

The novel method reduces $CO_2$ in a three-step reaction cycle, in which a binuclear metal-organic compound converts $CO_2$ to oxalate in a redox cycle under mild conditions. In one embodiment, a novel copper(II) complex $[Cu_2L_2X_2]^{2+}$ (L=m-xylylene-bis(pyridyltriazole); $X=NO_3$, Cl) is reduced to its Cu(I) counterpart. This reduction may be performed either electrochemically or with a mild reducing agent such as sodium ascorbate. The $[Cu_2L_2X_2]^{2+}$ complex selectively reacts with $CO_2$ to reduce it to oxalate, in an oxalate-bridged binuclear complex $[Cu_2L_2(\mu-C_2O_4)]^{2+}$. The bound oxalate ion may be released as oxalic acid by treatment with a strong acid such as HCl or $HNO_3$, thus regenerating the "empty" $[Cu_2L_2X_2]^{2+}$ complexes and completing the cycle.

The novel metal-organic system will reduce $CO_2$ to oxalate under mild reaction conditions. The binuclear Cu complex provides a unique environment that promotes binding and reduction of two $CO_2$ molecules to produce one oxalate. Although $CO_2$ is fixed relatively slowly, the Cu(I) dimer selectively reacts with $CO_2$ instead of $O_2$, a distinct advantage for a simple-to-operate process. Oxalic acid is readily released from the product.

The binuclear metallacyclic copper complex selectively captures $CO_2$ from air (or other streams) and reduces it to oxalate in an oxalate-bridged complex. This complex releases oxalic acid when treated with dilute mineral acid, regenerating the "empty" macrocycle and completing the cyclic process. The complex reacts both with pure $CO_2$, and with $CO_2$ in concentrations typical of those in air.

In an alternative embodiment, we have used vitamin C (sodium ascorbate) as a reducing agent to yield the copper(I)

complex that may then be used to reduce $CO_2$. Sodium ascorbate is a milder reagent and is easier to use than many other reducing agents.

METHODS

Example 1. Equipment and Materials

All commercially available reagents and solvents were purchased from Aldrich or Alfa Aesar, and were used without further purification. $^1$H Nuclear Magnetic Resonance (NMR) spectra were recorded on a Bruker AV-400 MHz spectrometer. ESI mass spectra were measured on an Agilent 6210 instrument. FTIR spectra were recorded on a Bruker Tensor 27 spectrometer in ATR mode. M-H-W Laboratories (Phoenix, Ariz.) performed elemental analyses. UV-visible spectra were recorded on an Aviv 14DS spectrometer. The samples were prepared in sealed flasks, and spectra were recorded using cuvettes connected to the flasks.

Cyclic voltammetry measurements were performed using a Princeton Applied Research Model 273A potentiostat/galvanostat with Power Suite 2.53 software. The measurements were carried out in 0.1 M $Bu_4NP F_6$ in dimethylformamide (DMF), with a glassy carbon working electrode, Ag/AgCl reference electrode, and Pt wire counter electrode.

The ligand m-xpt was synthesized following the procedure of Pokharel, U. R., Fronczek, F. R. & Maverick, A. W. Cyclic pyridyltriazole-Cu(II) dimers as supramolecular hosts. *Dalton Trans.* 42, 14064-14067, doi:10.1039/C3dt52208c (2013).

Example 2. $[Cu_2(m\text{-}xpt)_2(NO_3)_2](PF_6)_2$, 1

To a stirred solution of $Cu(NO_3)_2 \cdot 3H_2O$ (0.612 g, 2.54 mmol) in acetonitrile (75 mL), m-xpt (1.00 g, 2.54 mmol) in chloroform (50 mL) was added dropwise. The reaction mixture was stirred at room temperature for 2 hours. The precipitate was collected by filtration, washed with acetonitrile and chloroform, and dried to yield a blue solid $[Cu_2(m\text{-}xpt)_2](NO_3)_2](NO_3)_2$ (1.57 g, 1.35 mmol). This solid was dissolved in water (200 mL), and an aqueous solution of $NH_4PF_6$ (1.32 g, 8.09 mmol) was added. The mixture was stirred for 10 min and filtered. The precipitate was collected, washed with water, and dried in air to give compound 1 (1.84 g, 84%) as a light-blue powder. ESI-MS: m/z 1349.078, $[Cu_2(m\text{-}xpt)_2(PF_6)_3]^+$ (calcd 1349.082). Anal. Calcd for $[Cu_2(m\text{-}xpt)_2(NO_3)](PF_6)_3H_2O$: C, 36.93, H, 2.68, N, 16.64. Found: C, 36.88, H, 2.92, N, 15.40.

Complexing the ligand m-xpt with $Cu(NO_3)_2$ gave the dimeric macrocycle $[Cu_2(m\text{-}xpt)_2(NO_3)_2](NO_3)_2$. Although the distance between the two Cu centers in this compound was appropriate for small-molecule guests, the compound was insoluble in common organic solvents. To improve solubility and to widen the scope of host-guest chemistry, we replaced two of the nitrate anions with the more hydrophobic $PF_6^-$. Metathesis gave $[Cu_2(m\text{-}xpt)_2(NO_3)_2](PF_6)_2$, Compound 1.

A stirred solution of complex 1 (200 mg, 0.14 mmol) in 20 mL of DMF was reduced to $[Cu_2(m\text{-}xpt)_2](PF_6)_2$, Compound 3, by adding sodium ascorbate (41 mg, 0.21 mmol) under nitrogen for ca. 1 hour.

The amount of nitrogen seen in the elemental analysis was consistently lower than expected. We postulate that this observation may be due to the presence of species such as $[Cu_2(m\text{-}xpt)_2](PF_6)_4$ in the product mixture. When the product was crystallized by vapor diffusion of diethyl ether into its solution in DMF with benzene, we isolated $[Cu_2(m\text{-}xpt)_2(NO_3)_2](PF_6)_2$, 1.

Figure 1:
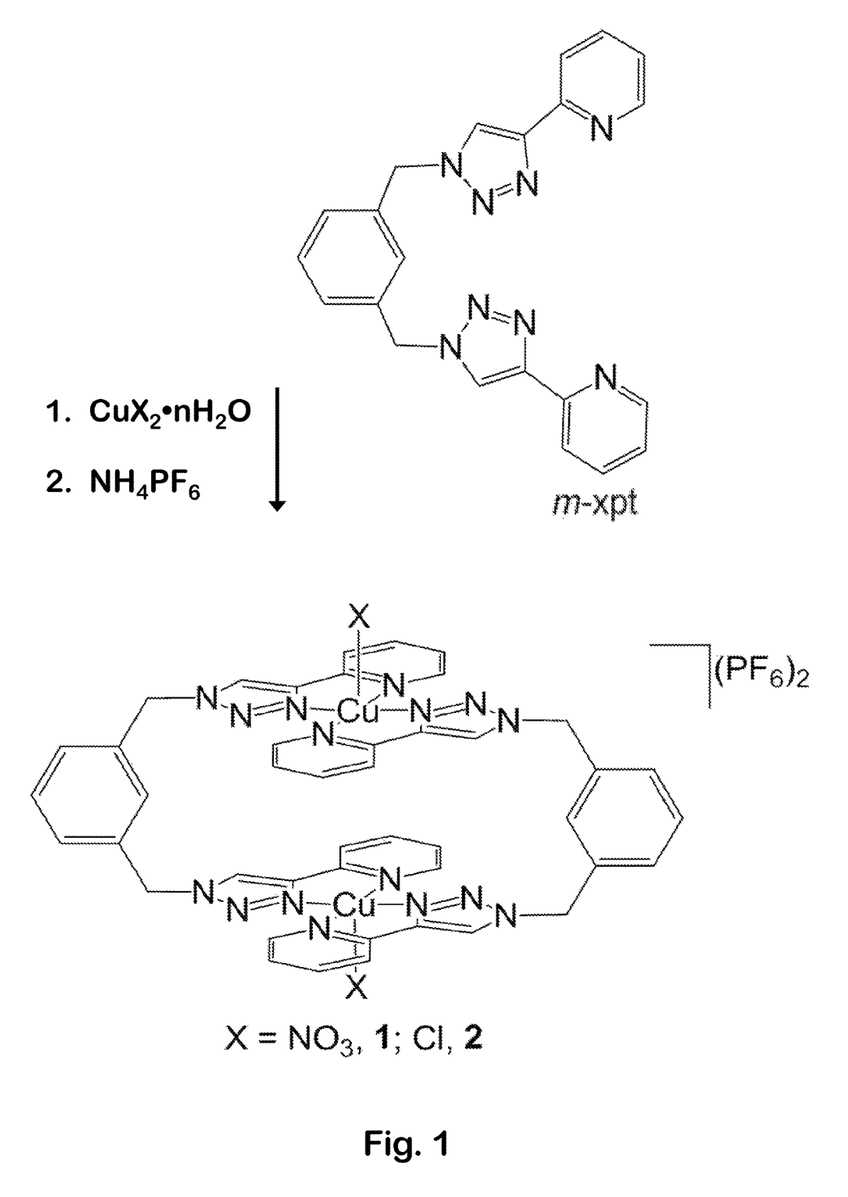
FIG. 1 depicts syntheses of complex 1 and complex 2.

FIG. 1 depicts the synthesis of complex 1, $[Cu_2(m\text{-}xpt)_2(NO_3)_2](PF_6)_2$. Cu . . . Cu distance as measured by x-ray diffraction was 6.843(2) Å

Example 3. $[Cu_2(m\text{-}xpt)_2Cl_2](PF_6)_2$, 2

Complexing m-xpt with $CuCl_2$ gave the dimeric macrocycle $[Cu_2(m\text{-}xpt)_2Cl_2]Cl_2$. This compound was also insoluble in common organic solvents, and we replaced the chloride anions with $PF_6^-$. Metathesis gave $[Cu_2(m\text{-}xpt)_2Cl_2](PF_6)_2$, Compound 2.

To a stirred solution of $[Cu_2(m\text{-}xpt)_2Cl_2]Cl_2$ (2.00 g, 1.86 mmol) in water (300 mL), excess $NH_4PF_6$ (1.82 g, 11.2 mmol) was added. The mixture was stirred for 10 minutes. The precipitate was collected by filtration, washed with water, and dried to give complex 2 (2.05 g, 86%) as a blue-green solid. A crystalline product was obtained from DMF by vapor diffusion of diethyl ether. ESI-MS: 1239.085 $[Cu_2(m\text{-}xpt)_2(PF_6)_2Cl]^+$ (calcd 1239.087). Anal. Calcd for $[Cu_2(m\text{-}xpt)_2Cl_2](PF_6)_2 \cdot 3DMF$: C, 42.55, H, 3.84, N, 17.79, Cl, 4.74. Found: C, 42.92, H, 3.49, N, 17.92, Cl, 5.21.

Example 4. $[Cu_2(m\text{-}xpt)_2](PF_6)_2$, 3

To a stirred solution of complex 1 (200 mg, 0.14 mmol) or complex 2 (178 mg, 0.14 mmol) in DMF (20 mL), sodium ascorbate (41 mg, 0.21 mmol) was added under $N_2$. After 1 hour, the yellow solution was slowly diffused with diethyl ether under nitrogen for 2 days. The resulting solid precipitate was collected by filtration, washed with diethyl ether, and dried to give complex 3 (164 mg, 85% from complex 1; 156 mg, 81% from complex 2). $^1$H NMR (DMSO-$d_6$, 400 MHz): 5.79 (s, 8H, $CH_2$), 7.43-7.49 (m, 12H, Ar), 8.12 (br, 8H, Ar), 8.43 (br, 4H, Ar), 9.23 (br, 4H, triazole). $^{13}$C NMR (DMSO-$d_6$, 125 MHz): 54.3, 122.1, 125.1, 125.9, 128.8, 129.3, 130.1, 136.0, 139.3, 146.0, 147.1, 149.5. ESI-MS: 1059.171 $[Cu_2(m\text{-}xpt)_2(PF_6)]^+$ (calcd 1059.154). Anal. Calcd for $[Cu_2(m\text{-}xpt)_2](PF_6)_2$: C, 43.82, H, 3.01, N, 18.58. Found: C, 43.58, H, 3.16, N, 17.92.

As we had observed for compound 1, compound 3 also gave microanalyses that were low in nitrogen. The addition of a small amount of ether to the formula gave better agreement; however, there were no signals attributable to ether or to other impurities in the compound's NMR spectrum.

Example 5. $[Cu_2(m\text{-}xpt)_2(\mu\text{-}C_2O_4)](PF_6)_2$, 4

We tested the selectivity of the reaction of complex 3 with $CO_2$, by generating the Cu(I) dimer. The yellow solutions that resulted from the previous syntheses were exposed to air to react with atmospheric $CO_2$, and also to allow slow evaporation of the DMF solvent. After 4 to 5 days, we isolated complex 4 in high yield (96% from complex 1; 69% from complex 2). We observed green octahedral crystals of $[Cu_2(m\text{-}xpt)_2(\mu\text{-}C_2O_4)](PF_6)_2$, 4, synthesized starting from $[Cu_2(m\text{-}xpt)_2(NO_3)_2](PF_6)_2$, 1 (crystal size ca. 0.3 mm). Both green and blue-green crystals were formed when complex 2 was used as the starting material. This conversion demonstrated selective reaction of $[Cu_2(m\text{-}xpt)_2]^{2+}$, 3, with $CO_2$ over $O_2$.

Both types of crystals were characterized by X-ray crystallography. The green crystals were found to be the desired oxalate-bridged dimer 4. The blue-green crystalline product was the starting Cu(II) dimer, $[Cu_2(m\text{-}xpt)_2Cl_2](PF_6)_2$. Both were washed with acetonitrile, which dissolved the blue-green crystals. Dimer 4 was collected by filtration (194 mg, 96% from complex 1; 138 mg, 69% from complex 2). FTIR $(cm^{-1})$: 1670 (s), 1645 (s), 1610 (s), 1454 (s), 839 (vs), 785 (vs), 715 (vs). Anal. Calcd for $[Cu_2(m\text{-}xpt)_2(\mu\text{-}C_2O_4)(PF_6)_2]\cdot2DMF$: C, 43.37, H, 3.50, N, 17.51. Found: C 43.48, H 3.52, N 17.58. The Cu . . . Cu separation, 5.4213(7) Å and the distances within the bridging oxalate ligand (C—C 1.544(7) Å; C—O 1.248(3) Å), were similar to those that have been observed for other $C_2O_4^{2-}$-bridged copper complexes.

Example 6. $[Cu_2(m\text{-}xpt)_2(\mu\text{-}^{13}C_2O_4)](PF_6)_2$

The Cu(I) complex 3 derived from complex 1 was transferred into a sealed flask connected to a cuvette. The reaction mixture was purged with nitrogen using four alternating cycles of vacuum and nitrogen. The reaction mixture showed no changes in the UV-vis spectrum after 48 hours. The $N_2$ was then replaced with $^{13}CO_2$. The yellow solution progressively turned green over a period of 128 hours, as $^{13}CO_2$ was added periodically to maintain the pressure at ca. 1 atm. After the reaction was complete, the solution was poured into a watch glass and left to crystallize by slow evaporation of DMF. The crystalline solid was washed with acetone.

Example 7. $[Cu_2(m\text{-}xpt)_2(\mu\text{-}C_2O_4)](PF_6)_2$, 4a

As a complementary reaction to that displacing bound oxalate from complex 4, we also tested the ability of empty macrocycles to accept oxalate ion as a guest. The reaction of complex 1 and 2 with tetrabutylammonium oxalate in acetonitrile yielded $[Cu_2(m\text{-}xpt)_2(\mu\text{-}C_2O_4)]^{2+}$, as confirmed by single crystal X-ray analysis.

We prepared $[Cu_2(m\text{-}xpt)_2(\mu\text{-}C_2O_4)]^{2+}$ from Cu(II) and oxalate as follows: To a stirred solution of complex 1 (200 mg, 0.14 mmol) or complex 2 (178 mg, 0.14 mmol) in acetonitrile (20 mL), tetrabutylammonium oxalate (80 mg, 0.15 mmol) was added. The mixture was stirred for 30 minutes and then left to crystallize by slow evaporation of the solvent. Yellow-green crystals formed, and were then washed with acetonitrile and air-dried to give 4a (178 mg, 87% from complex 1; 147 mg, 72% from complex 2). X-ray analysis showed that these crystals were the acetonitrile solvate of $[Cu_2(m\text{-}xpt)_2(\mu\text{-}C_2O_4)](PF_6)_2$, 4a (Cu . . . Cu=5.462(2) Å), which is isostructural with the DMF solvate 4. (See Table 2 for data and refinement parameters.)

Example 8. $[Cu_2(m\text{-}xpt)_2(H_2O)_2](NO_3)_4$, 5

Bound oxalate was removed from $[Cu_2(m\text{-}xpt)_2(\mu\text{-}C_2O_4)](PF_6)_2$, 4 to regenerate the "empty" Cu(II) macrocycle $[Cu_2(m\text{-}xpt)_2]^{4+}$. Crystallization from $DMF/H_2O$ gave the "empty" host complexes $[Cu_2(m\text{-}xpt)_2Cl_2]Cl_2$ and $[Cu_2(m\text{-}xpt)_2(H_2O)_2](NO_3)_4$, 5, from the reaction of complex 4 with HCl and $HNO_3$, respectively. The yields of empty complexes after acid treatment were nearly quantitative: 94% (HCl) and 96% ($HNO_3$).

HCl(aq) (8 eq) or $HNO_3$(aq) (8 eq) (2 mL of 0.32 M, 0.64 mmol) was added to a stirred suspension of complex 4 (100 mg, 0.07 mmol) in methanol (50 mL). The solid dissolved, giving a greenish-yellow solution (HCl) or a blue solution ($HNO_3$), which deposited a green or blue-green precipitate after stirring for an additional 3 hours. The mixture was filtered and the solid was re-dissolved in a mixture of water and DMF (4:1 v/v). The solution was poured into a watch glass and left to stand for slow evaporation. After 4 to 5 days, a blue-green (HCl) or blue ($HNO_3$) crystalline product had formed. These crystals were washed with ca. 5 mL methanol and were air-dried. X-ray analysis of the products revealed the formation of empty Cu(II) macrocycles: $[Cu_2(m\text{-}xpt)_2Cl_2]Cl_2\cdot4DMF$ (with HCl; 92 mg, 94%) or $[Cu_2(m\text{-}xpt)_2(H_2O)_2](NO_3)_4\cdot4DMF$, 5 (with $HNO_3$; 81 mg, 96%).

The filtrate from the above reaction was evaporated to dryness. The solid was dissolved in water (2 mL). The solution was neutralized with KOH(aq) and extracted with chloroform. The aqueous phase was acidified with HCl and again evaporated to dryness to give oxalic acid as a white solid which was characterized by $^{13}C$ NMR (163.2 ppm) and FTIR spectroscopy ($v_{CO}$=1668 $cm^{-1}$; with $^{13}CO_2$, 1642 $cm^{-1}$).

$[Cu_2(m\text{-}xpt)_2(H_2O)_2](NO_3)_4$, 5, formed by removal of oxalate from $[Cu_2(m\text{-}xpt)_2(\mu\text{-}C_2O_4)](PF_6)_2$, 4 had a Cu . . . Cu distance=7.2441(8) Angstrom Anal. Calcd for $[Cu_2(m\text{-}xpt)_2(H_2O)_2](NO_3)_4\cdot2H_2O$: C 42.76, H 3.59, N 22.66. Found: C 42.38, H 3.55, N 21.86.

Results

Example 9. Cyclic Voltammetry

Figure 2:
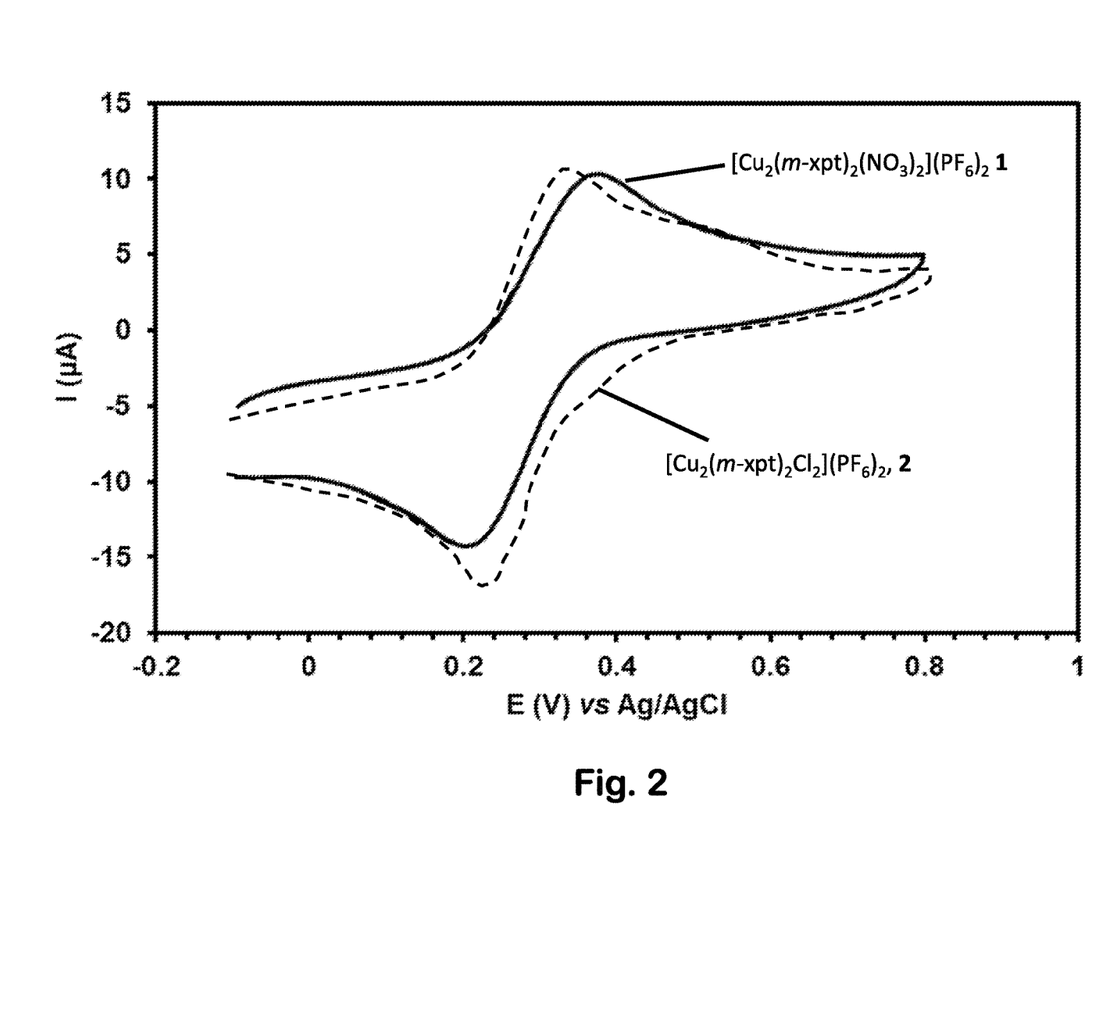
FIG. 2 depicts cyclic voltammograms for complex 1 and complex 2.

Cyclic voltammetry of complex 1 and complex 2 in DMF showed quasi-reversible waves at ca. 0.28 V vs. Ag/AgCl (−0.27 V for complex 1 and −0.28 V for complex 2 vs. $Fc/Fc^+$). FIG. 2 shows cyclic voltammograms of $[Cu_2(m\text{-}xpt)_2(NO_3)_2](PF_6)_2$ and $[Cu_2(m\text{-}xpt)_2Cl_2](PF_6)_2$ in DMF containing 0.1 M $Bu_4NPF_6$. Data were recorded on a static glassy carbon disc working electrode with a Pt wire auxiliary electrode and Ag/AgCl reference electrode at 25° C. at a scan rate of 50 mV $s^{-1}$.

Figure 3:
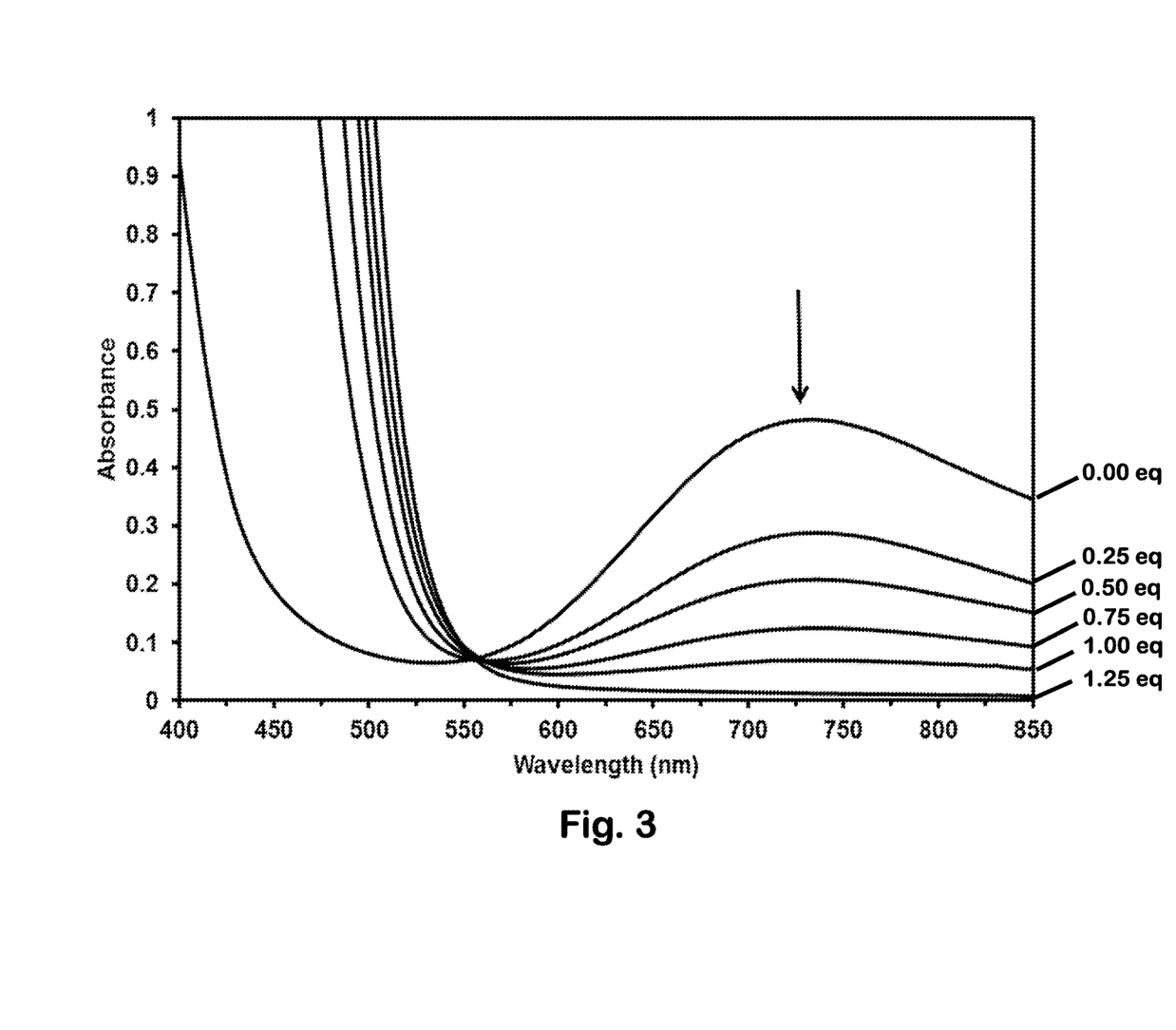
FIG. 3 depicts a portion of the UV-Vis absorption spectrum of a 3.76 mM solution of complex 1 with increasing amounts of added sodium ascorbate.
Figure 4:
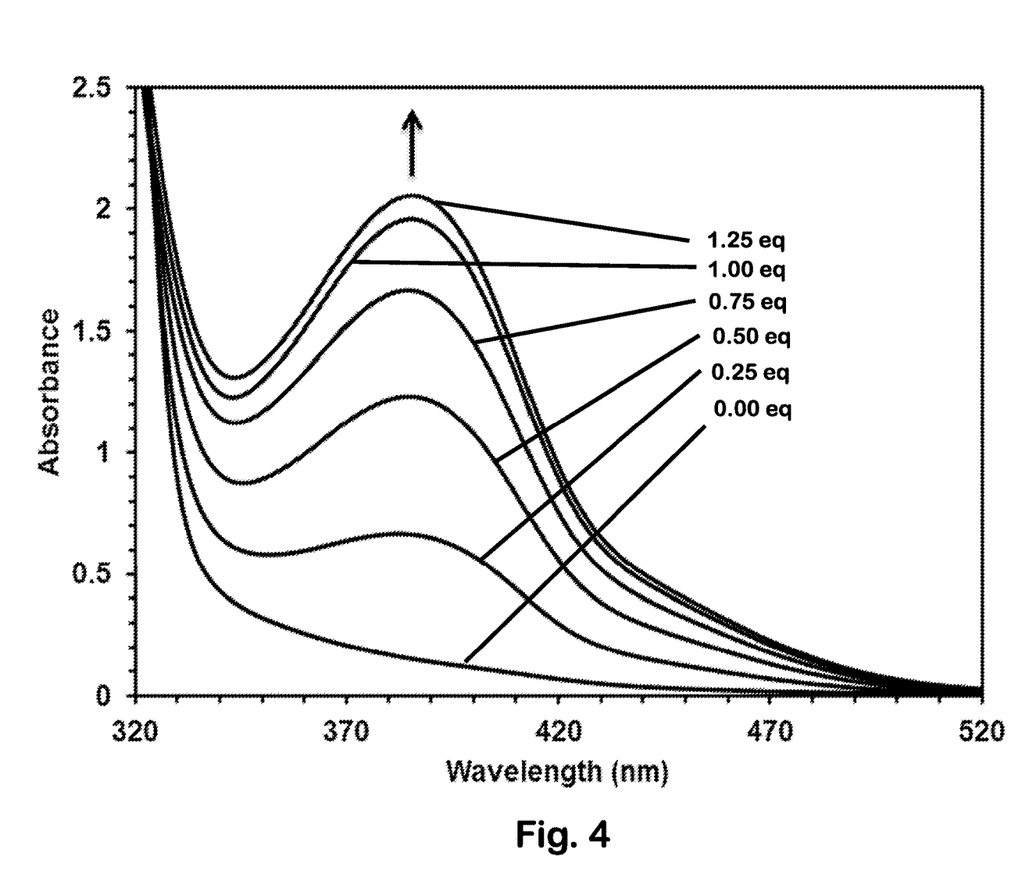
FIG. 4 depicts a portion of the UV-Vis absorption spectrum of a 0.20 mM solution of complex 1 with increasing amounts of added sodium ascorbate.

We investigated the reactivity of the Cu(I) dimers obtained by reducing complex 1 or 2. For chemical reduction of Cu(II) to Cu(I), we used sodium ascorbate to produce Cu(I) catalysts in situ for an azide-alkyne cyclization reaction. Treatment of complex 1 or 2 with sodium ascorbate in DMF under $N_2$ gave a yellow copper(I) complex. During the reduction of complex 1 or 2 to Cu(I), the Cu(II) d-d electronic absorption band disappeared, and an intense new band at 384 nm appeared (FIGS. 3 and 4). We attributed the 384 nm ($\epsilon$=1.05×10$^4$ $M^{-1}$ $cm^{-1}$) band to a metal-to-ligand charge transfer transition in the macrocyclic Cu(I) complex $[Cu_2(m\text{-}xpt)_2](PF_6)_2$, 3. This new compound was surprisingly stable in air for several days in the solid state.

Solutions of 3, generated by in situ reduction of complex 1 or 2 with sodium ascorbate in DMF, reacted with $CO_2(g)$ to produce the oxalate-bridged Cu(II) dimer [Cu$_2$(m-xpt)$_2$(μ-C$_2$O$_4$)](PF$_6$)$_2$, 4. The progress of the reaction was monitored by electronic absorption spectroscopy. We examined both the appearance of the Cu(II) d-d band in dimer 4 ($\lambda_{max}$=751 nm, $\epsilon$=98 M$^{-1}$ cm$^{-1}$) and the disappearance of the Cu(I) metal-to-ligand charge transfer band at 384 nm, under CO$_2$ maintained at 1 atm. The reaction was nearly complete after 128 h.

FIG. 3 depicts a portion of the UV-Vis spectrum of a 3.76 mM solution of [Cu$_2$(m-xpt)$_2$(NO$_3$)$_2$(PF$_6$)$_2$, 1 in DMF with increasing amounts of added sodium ascorbate: 0 to 1.25 eq.

FIG. 4 depicts a portion of the UV-Vis spectrum of a 0.20 mM solution of [Cu$_2$(m-xpt)$_2$(NO$_3$)$_2$(PF$_6$)$_2$, 1 in DMF with increasing amounts of added sodium ascorbate: 0 to 1.25 eq. $\lambda_{max}$=384 nm.

Figure 5:
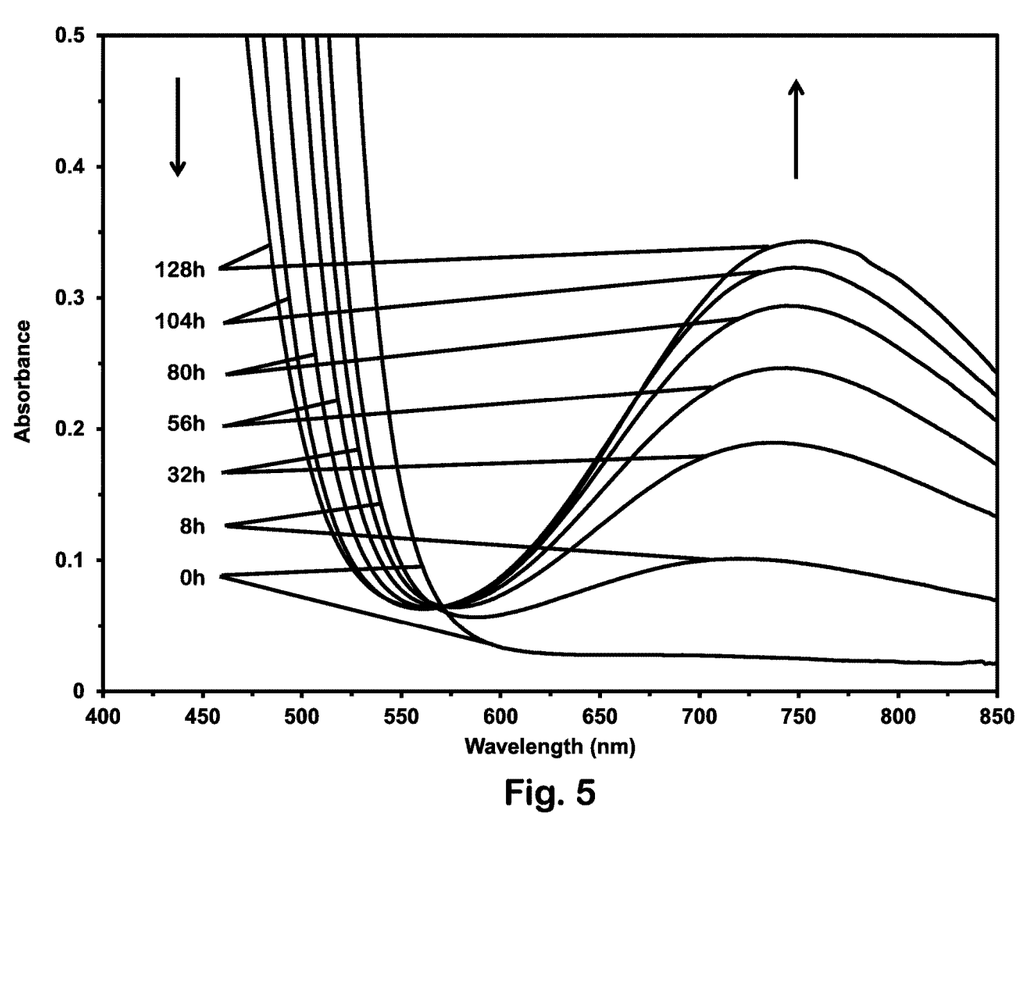
FIG. 5 depicts spectral changes over time during reduction of $CO_2$ to oxalate.

FIG. 5 depicts spectral changes over time during reduction of CO$_2$ to oxalate. A 3.76 mM solution of [Cu$_2$(m-xpt)$_2$](PF$_6$)$_2$, 3, generated in situ from complex 1 in DMF using sodium ascorbate, was kept under N$_2$ for 48 h, followed by oxidation by CO$_2$. The spectra, measured after 8 h and then every 24 h to 128 h, demonstrated gradual formation of [Cu$_2$(m-xpt)$_2$(μ-C$_2$O$_4$)]$^{2+}$, 4 ($\lambda_{max}$=751 nm).

Figure 6:
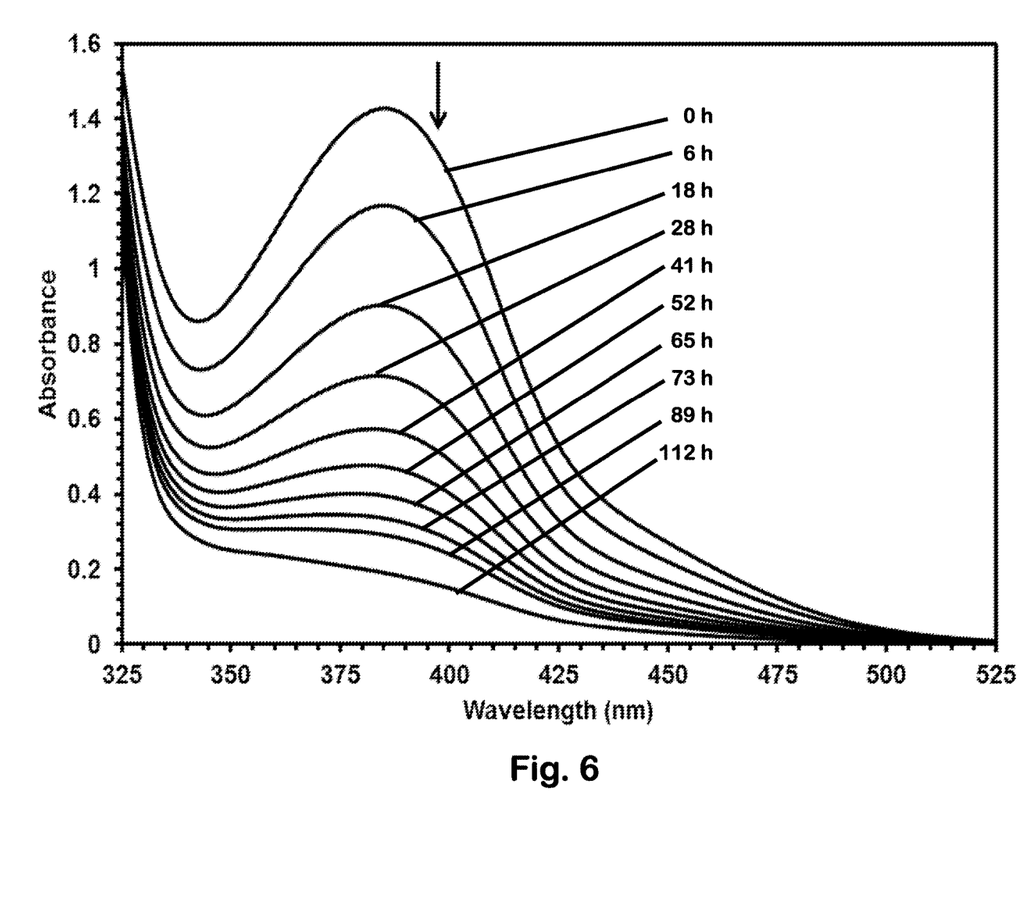
FIG. 6 depicts a portion of the UV-Vis absorption spectrum of a 0.12 mM solution of complex 3 over time during its reaction with $CO_2$.

FIG. 6 depicts a portion of the UV-Vis spectrum over time of a 0.12 mM solution of [Cu$_2$(m-xpt)$_2$](PF$_6$)$_2$, 3, in DMF during its reaction with CO$_2$: 0 h (at top) to 112 h at bottom).

Example 10. IR Spectra

Figure 7A:
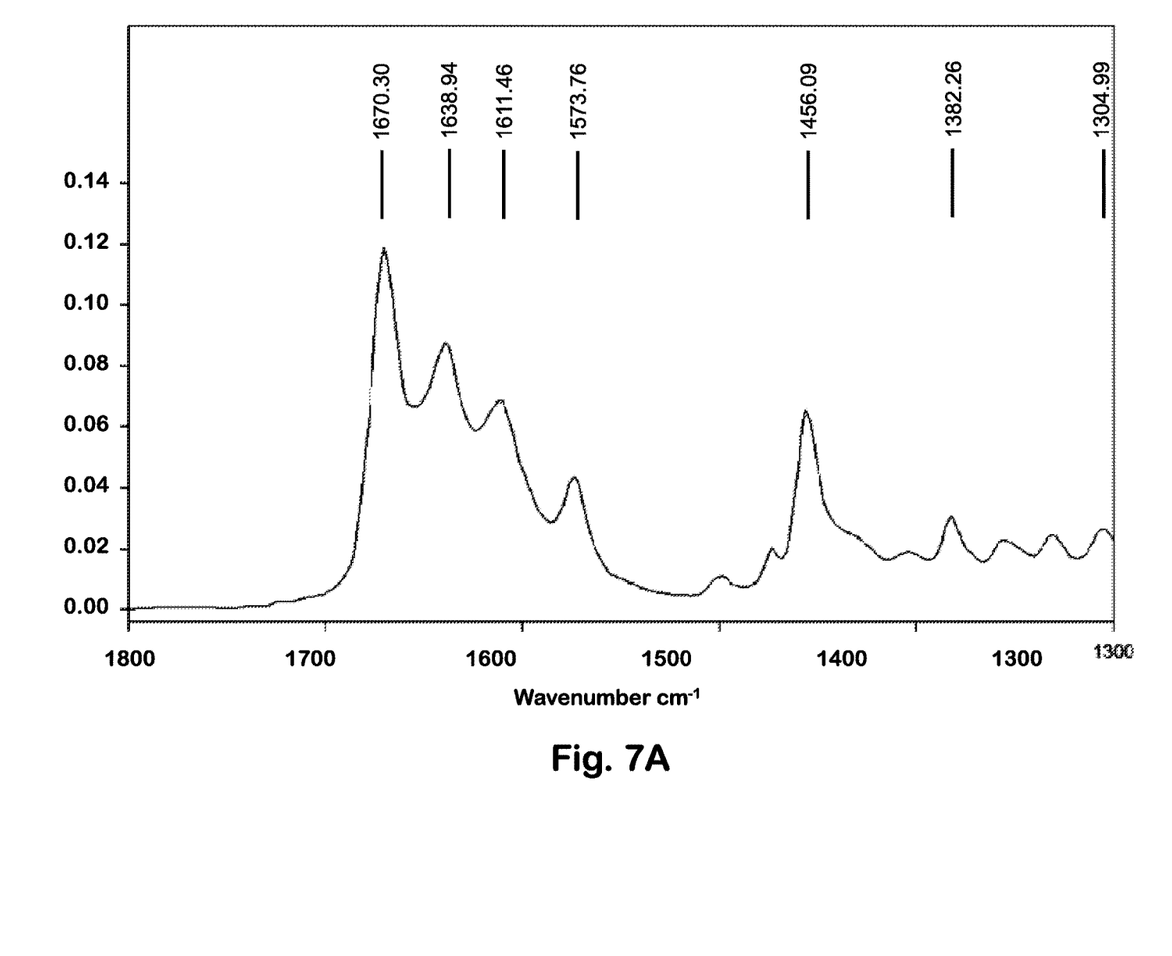
FIGS. 7(a) and (b) depict the IR spectra of $[Cu_2(m\text{-}xpt)_2(\mu\text{-}C_2O_4)](PF_6)_2$ and $[Cu_2(m\text{-}xpt)_2(\mu\text{-}^{13}C_2O_4)](PF_6)_2$, respectively.
Figure 7B:
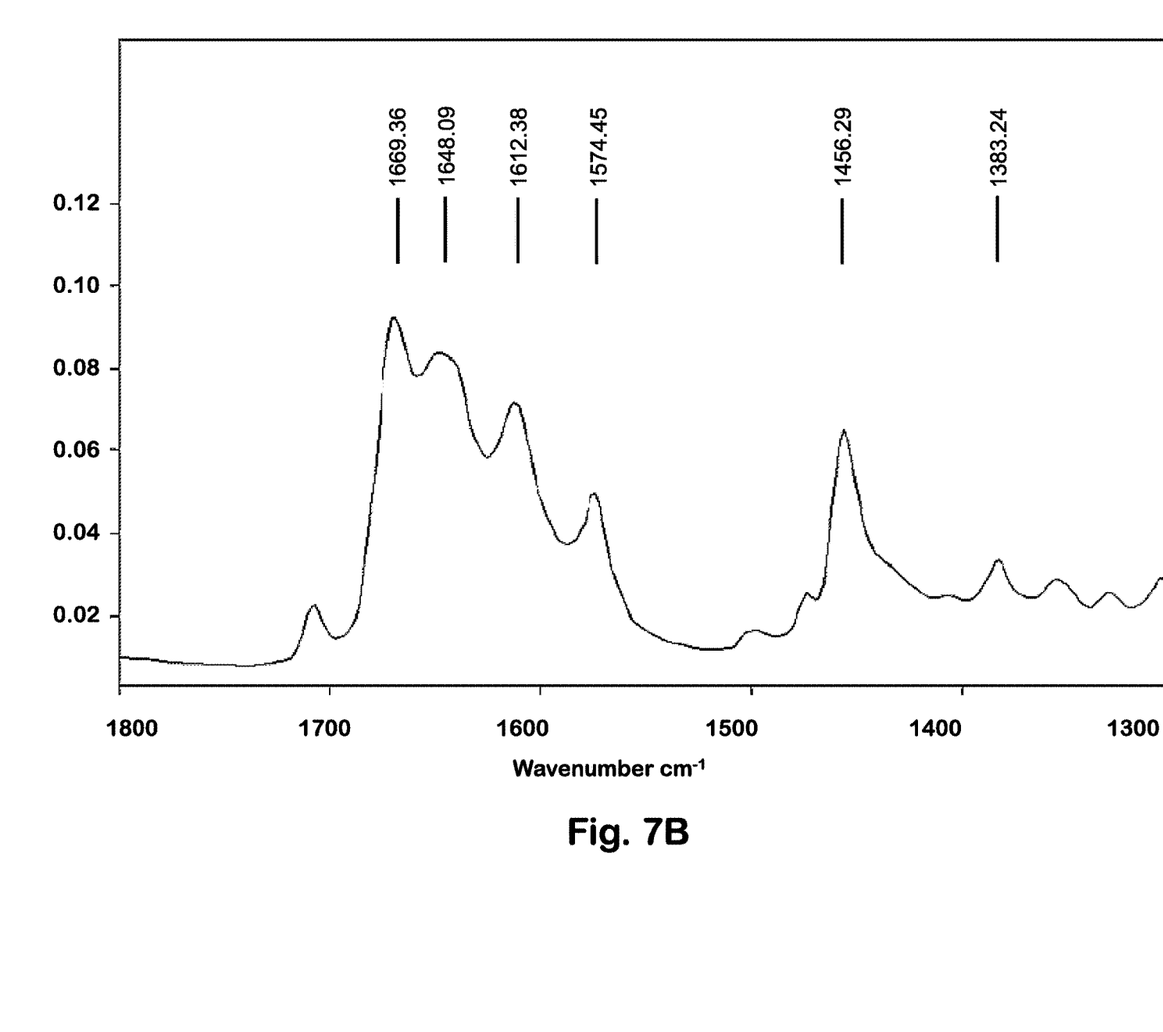
Figure 8:
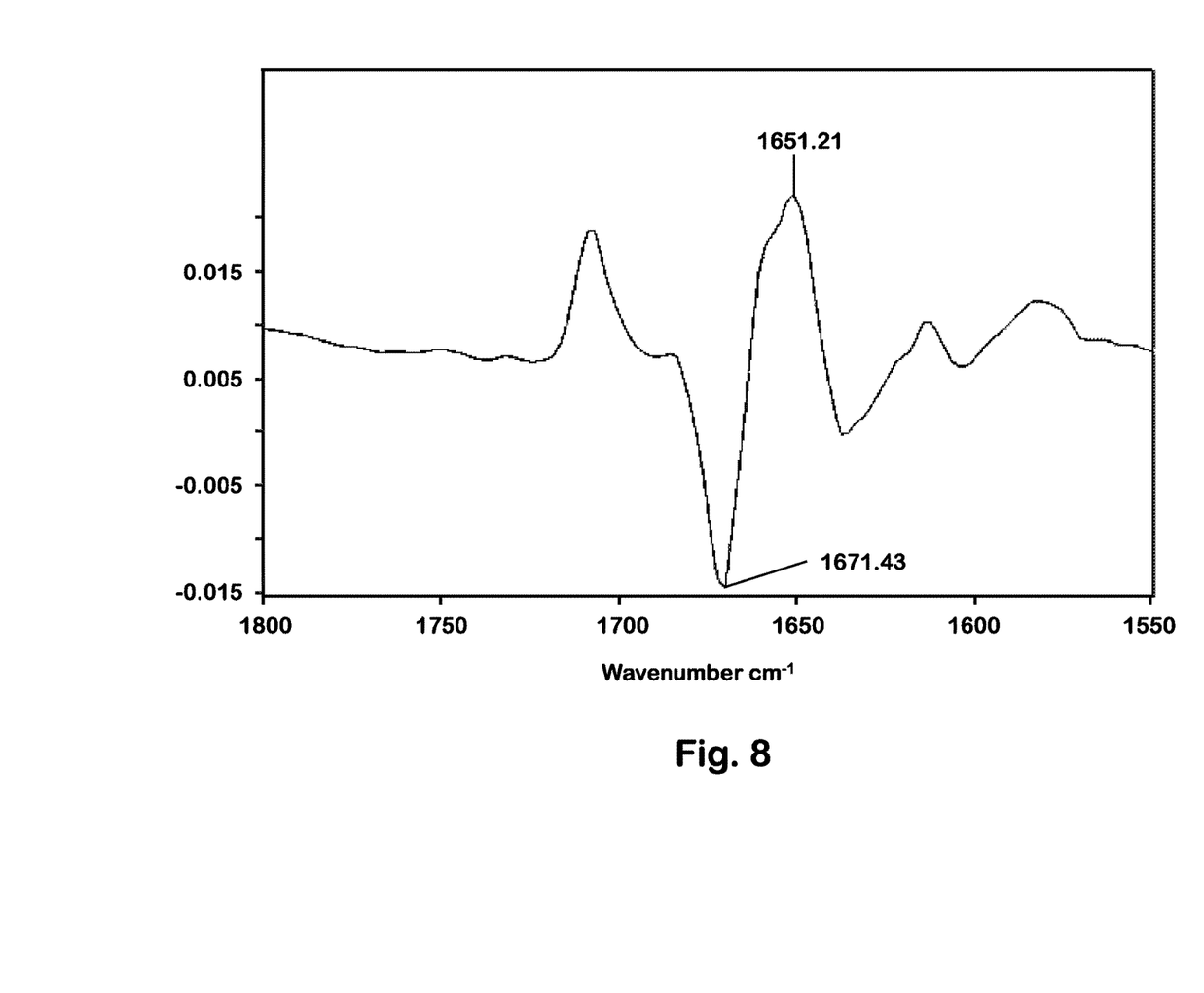
FIG. 8 depicts the difference between the IR spectra of $[Cu_2(m\text{-}xpt)_2(\mu\text{-}C_2O_4)](PF_6)_2$ and $[Cu_2(m\text{-}xpt)_2(\mu\text{-}^{13}C_2O_4)](PF_6)_2$.

IR spectra of [Cu$_2$(m-xpt)$_2$(μ-C$_2$O$_4$)](PF$_6$)$_2$ and [Cu$_2$(m-xpt)$_2$(μ-$^{13}$C$_2$O$_4$)](PF$_6$)$_2$ are shown in FIGS. 7(a) and (b), respectively. The IR spectrum of dimer 4 showed $v_{CO}$=1670 cm$^{-1}$; an analogous measurement with $^{13}$CO$_2$ gave $v_{CO}$=1651 cm$^{-1}$. A difference spectrum showing $v_{13CO}$=1651 cm$^{-1}$ is depicted in FIG. 8.

Example 11. X-Ray Data Collection and Structure Determination

Intensity data were collected at low temperature on a Bruker Kappa Apex-II DUO CCD diffractometer fitted with an Oxford Cryostream chiller. MoKα ($\lambda$=0.71073 Å) radiation with a TRIUMPH curved graphite monochromator was used for 2, 4, and 4a. CuKα ($\lambda$=1.54184 Å) radiation from an I μS microfocus source with QUAZAR multilayer optics was used for 1 and 5. Data reduction included absorption corrections by a multiscan method, with SADABS, or TWINABS for 5.

Structures were determined both by direct methods and by difference Fourier techniques, and were then refined by full-matrix least squares using SHELXL-97. All non-hydrogen atoms were refined anisotropically, except for the minor component in a disordered nitrate in 1 and 5, C atoms in 2, and the minor component of the disordered PF$_6^-$ anion in 1 (vide infra).

The crystal structure of dimer 4 contained dimeric cationic complexes with crystallographically imposed 2/m (C$_{2h}$) symmetry. For 2, low data quality did not allow anisotropic refinement of the C atoms. Disordered solvents were removed using the SQUEEZE procedure for 2, resulting in non-integral solvent stoichiometry. Normal refinement procedures for 2 led to several unreasonable distances within the m-xpt ligands. Therefore, for the final refinement, the two sets of ligand atoms were restrained to yield similar bond distances and angles.

For 4 and 4a, the PF$_6^-$ anion was disordered in two orientations. A single solvent molecule (DMF for the crystals prepared by reaction of Cu(I) (3) with CO$_2$; CH$_3$CN for the crystals prepared by reaction of Cu(II) (1 or 2) with oxalate) was disordered across a mirror plane.

The crystal of 5 was a nonmerohedral twin by 180° rotation about real axis [−1 0 1]. Refinement was versus HKLF5 data, and the twin components were present approximately 52/48%. This structure had a disorder involving a nitrate ion in two positions and a partially occupied water molecule associated with one of them. All H atoms were placed in idealized positions, except for water hydrogen atoms. Water H atoms were refined with restrained O—H distances, but the H atoms of the water molecule in the nitrate/water disorder of 5 could not be located.

Example 12. Crystal Data and Structure Refinement Parameters

TABLE 1

Crystal Data and Structure Refinement Parameters for 1 and 2.

| Compound | 1 | 2 |
|---|---|---|
| deposition no. | CCDC 1000457 | CCDC 1000458 |
| formula | [Cu$_2$(m-xpt)$_2$(NO$_3$)$_2$](PF$_6$)$_2$ · 3.5CH$_3$CN | [Cu$_2$(m-xpt)$_2$Cl$_2$](PF$_6$)$_2$ · 4.44C$_3$H$_7$NO |
| M | 1329.93 | 1601.17 |
| crystal system | Monoclinic | Orthorhombic |
| space group | P2$_1$/c | Pna2$_1$ |
| a/Å | 11.4090(16) | 13.810(2) |
| b/Å | 12.8455(18) | 19.380(3) |
| c/Å | 23.411(3) | 24.711(3) |
| β/deg | 108.575(5) | 90 |
| V/Å$^3$ | 3252.3(8) | 6613.6(16) |
| Z | 2 | 4 |
| T/K | 100.0(5) | 90.0(5) |
| D$_{calc}$/g cm$^{-3}$ | 1.358 | 1.608 |
| crystal dimensions/mm | 0.35 × 0.17 × 0.10 | 0.04 × 0.14 × 0.31 |
| Radiation | CuKα | MoKα |
| θ limits/deg | 3.98-59.20 | 1.65-25.71 |
| reflns, measd/unique/obsd | 22792/4639/3982 | 52940/12074/7203 |
| F(000) | 1340 | 3278 |
| μ/mm$^{-1}$ | 2.066 | 0.871 |
| R$_{int}$ | 0.0468 | 0.0525 |
| R[I>2σ(I)] | 0.1013 | 0.0830 |
| R$_W$ (all data) | 0.3540 | 0.2384 |
| GOF | 1.624 | 1.053 |

TABLE 2

Crystal Data and Structure Refinement Parameters for 4, 4a, and 5.

| Compound | 4 | 4a | 5 |
|---|---|---|---|
| deposition no. | CCDC 984468 | CCDC 984469 | CCDC 984470 |
| formula | [C$_{46}$H$_{36}$Cu$_2$N$_{16}$O$_4$](PF$_6$)$_2$ · 2C$_3$H$_7$NO | [C$_{46}$H$_{36}$Cu$_2$N$_{16}$O$_4$](PF$_6$)$_2$ · 4CH$_3$CN | [C$_{44}$H$_{40}$Cu$_2$N$_{16}$O$_2$](NO$_3$)$_4$ · 2C$_3$H$_7$NO · 3.34H$_2$O |
| M | 1440.12 | 1458.14 | 1406.50 |
| crystal system | Orthorhombic | Orthorhombic | Monoclinic |

TABLE 2-continued

Crystal Data and Structure Refinement Parameters for 4, 4a, and 5.

| Compound | 4 | 4a | 5 |
|---|---|---|---|
| space group | Cmca | Cmca | P2$_1$/n |
| a/Å | 24.1471(17) | 24.461(7) | 11.4361(13) |
| b/Å | 11.7107(7) | 11.959(3) | 22.691(3) |
| c/Å | 20.5949(12) | 20.008(5) | 11.9848(13) |
| β/deg | 90 | 90 | 106.847(5) |
| V/Å$^3$ | 5823.8(6) | 5853(3) | 2976.6(6) |
| Z | 4 | 4 | 2 |
| T/K | 100.0(5) | 100.0(5) | 100.0(5) |
| D$_{calc}$/g cm$^{-3}$ | 1.642 | 1.655 | 1.569 |
| Crystal dimensions mm | 0.45 × 0.17 × 0.04 | 0.30 × 0.22 × 0.13 | 0.12 × 0.19 × 0.21 |
| radiation | MoKα | MoKα | CuKα |
| θ limits/deg | 1.69-30.05 | 2.04-30.23 | 4.32-69.67 |
| reflns, measd/unique/obsd | 44218/4357/3592 | 31270/4418/3607 | 52513/14803/12358 |
| F(000) | 2928 | 2960 | 1455 |
| μ/mm$^{-1}$ | 0.891 | 0.886 | 1.691 |
| R$_{int}$ | 0.0310 | 0.0447 | 0.0741 |
| R[I>2σ(I)] | 0.0527 | 0.0346 | 0.0637 |
| R$_W$ (all data) | 0.1531 | 0.0900 | 0.1928 |
| GOF | 1.033 | 1.031 | 1.024 |

In one embodiment, a compound in accordance with the present invention is a binuclear compound having the structure [Cu$_2$L$_2$(μ-C$_2$O$_4$)$_p$]X$_n^{m+}$ wherein:

L is m-xylylenebis(pyridyltriazole);

X is a monovalent anion; wherein if n is 2 or 4, the various X anions may be the same or different; as illustrative examples, X may be chloride, other halide, halogen, nitrate, or any other common monovalent anion;

p is 0 or 1;

n is 0, 2, or 4; and m is 0, 2, or 4.

In another embodiment, a compound in accordance with the present invention is a binuclear compound having the structure [Cu$_2$L$_2$(μ-C$_2$O$_4$)$_p$]X$_n^{m+}$ wherein:

X is a monovalent anion; wherein if n is 2 or 4, the various X anions may be the same or different; as illustrative examples, X may be chloride, other, halogen, nitrate, or any other common monovalent anion;

p is 0 or 1;

n is 0, 2, or 4;

m is 0, 2, or 4;

L is:

R$^1$ may be used to modify the properties of the internal cavity where CO$_2$ binds, or to control access to the cavity. R$^1$ may be, for example, H, C$_1$-C$_4$ substituted or unsubstituted alkyl, —NH$_2$, —OH, —CO$_2$H;

R$^2$, R$^3$, and R$^4$, particularly R$^3$, may be used to enhance the solubility of the complexes in certain solvents. For example, R$^3$=OCH$_2$CH$_2$CH$_2$CH$_3$ is expected to increase solubility in nonpolar solvents such as toluene. R$^2$, R$^3$, and R$^4$ may, for example, be independently chosen from H, substituted or unsubstituted C$_1$-C$_8$ alkyl, substituted or unsubstituted aryl, —OH, —OC$_k$H$_{2k+1}$, —O(CH$_2$CH$_2$O)$_k$CH$_3$, —O(CH$_2$CH$_2$O)$_k$C$_2$H$_5$, —N(CH$_3$)$_3^+$, —SO$_3^-$, —NO$_2$, —CN (k=1-8);

R$^5$, R$^6$, R$^7$, and R$^8$ may be used to modify solubility, or to modify the electron-donating ability of the ligand as it coordinates to the Cu ions, or both. Modifying the electron-donating ability may be useful in altering the reducing strength of the Cu(I) complexes, which will in turn affect the rate of reaction of Cu(I) with CO$_2$. R$^5$, R$^6$, R$^7$, and R$^8$ may, for example, be independently chosen from: H; —OCH$_3$, —N(CH$_3$)$_2$ (electron-releasing); halogen, —NO$_2$, —CN (electron-withdrawing); or substituted or unsubstituted C$_1$-C$_8$ alkyl, substituted or unsubstituted aryl, —OH, —OC$_j$H$_{2j+1}$, —O(CH$_2$CH$_2$O)$_j$CH$_3$, —O(CH$_2$CH$_2$O)$_j$C$_2$H$_5$, —N(CH$_3$)$_3^+$, —SO$_3^-$, (j=1-8).

The complete disclosures of all references cited in the specification are hereby incorporated by reference in their entirety, as is the complete disclosure of priority application Ser. No. 61/890,403. Also incorporated by reference is the complete disclosure of the following work by the present inventors, including its associated supplemental information: Pokharel, U. R., Fronczek, F. R. & Maverick, A. W. Cyclic pyridyltriazole-Cu(II) dimers as supramolecular hosts. *Dalton Trans.* 42, 14064-14067, doi:10.1039/C3dt52208c (2013). In the event of an otherwise irresolvable conflict, however, the disclosure of the present specification shall control.

What is claimed:

1. A binuclear compound having the structure [Cu$_2$L$_2$(μ-C$_2$O$_4$)$_p$]X$_n^{m+}$ wherein:

p is 0 or 1;

n is 0, 2, or 4;

m is 0, 2, or 4;

X is a monovalent anion; wherein if n is 2 or 4, the various X anions may be the same or different; and
L is:

wherein:
$R^1$ is chosen from the group consisting of H, $C_1$-$C_4$ substituted or unsubstituted alkyl, —$NH_2$, —OH, and —$CO_2H$;
$R^2$, $R^3$, and $R^4$ are independently chosen from the group consisting of H, substituted or unsubstituted $C_1$-$C_8$ alkyl, substituted or unsubstituted arene or heteroarene radical, —OH, —$OC_kH_{2k+1}$, —$O(CH_2CH_2O)_kCH_3$, —$O(CH_2CH_2O)_kC_2H_5$, $N(CH_3)_3^+$, —$SO_3^-$, —$NO_2$, and —CN; wherein k is 1, 2, 3, 4, 5, 6, 7, or 8;
$R^5$, $R^6$, $R^7$, and $R^8$ are independently chosen from the group consisting of H, —$OCH_3$, —$N(CH_3)_2$, halogen, —$NO_2$, —CN, substituted or unsubstituted $C_1$-$C_8$ alkyl, substituted or unsubstituted arene or heteroarene radical, —OH, $OC_jH_{2j+1}$, —$O(CH_2CH_2O)_jCH_3$, —$O(CH_2CH_2O)_jC_2H_5$, —$N(CH_3)_3^+$, —$SO_3^-$, —$NO_2$, and —CN, wherein j is 1, 2, 3, 4, 5, 6, 7, or 8;
and wherein:
said compound has the property that it can cycle between a Cu(I) form of the compound and a Cu(II) form of the compound, as a function of redox potential;
and wherein:
the Cu(I) form of the compound has the property that it can react with carbon dioxide to reduce carbon dioxide to oxalate, whereby the compound is oxidized to the Cu(II) form of the compound.

2. The compound of claim 1, wherein L is m-xylylenebis (pyridyltriazole).

3. The compound of claim 1, wherein said compound is selected from the group consisting of $[Cu_2L_2(\mu-C_2O_4)]^{2+}$; $[Cu_2L_2(\mu-C_2O_4)](PF_6)_2$; $[Cu_2L_2(NO_3)_2](PF_6)_2$; $[Cu_2L_2(NO_3)_2](NO_3)_2$; $[Cu_2L_2](PF_6)_2$; $[Cu_2L_2Cl_2]Cl_2$; $[Cu_2L_2Cl_2](PF_6)_2$; $[Cu_2L_2]^{2+}$; and $[Cu_2L_2]^{4+}$.

4. The compound of claim 3, wherein L is m-xylylenebis (pyridyltriazole).

5. A method for reducing carbon dioxide to oxalate; said method comprising the sequential steps of:
(a) reacting carbon dioxide with the Cu(I) form of the compound of claim 1 to produce oxalate complexed to the Cu(II) form of the compound of claim 1;
(b) reacting the oxalate complex from step (a) with a mineral acid to liberate oxalate from the Cu(II) form of the compound of claim 1;
(c) reducing the Cu(II) form of the compound of claim 1 from step (b) to regenerate the Cu(I) form of the compound of claim 1.

6. A method for reducing carbon dioxide to oxalate; said method comprising the sequential steps of:
(a) reacting carbon dioxide with the Cu(I) form of the compound of claim 2 to produce oxalate complexed to the Cu(II) form of the compound of claim 2;
(b) reacting the oxalate complex from step (a) with a mineral acid to liberate oxalate from the Cu(II) form of the compound of claim 2;
(c) reducing the Cu(II) form of the compound of claim 2 from step (b) to regenerate the Cu(I) form of the compound of claim 2.

7. A method for reducing carbon dioxide to oxalate; said method comprising the sequential steps of:
(a) reacting carbon dioxide with the Cu(I) form of the compound of claim 3 to produce oxalate complexed to the Cu(II) form of the compound of claim 3;
(b) reacting the oxalate complex from step (a) with a mineral acid to liberate oxalate from the Cu(II) form of the compound of claim 3;
(c) reducing the Cu(II) form of the compound of claim 3 from step (b) to regenerate the Cu(I) form of the compound of claim 3.

8. A method for reducing carbon dioxide to oxalate; said method comprising the sequential steps of:
(a) reacting carbon dioxide with the Cu(I) form of the compound of claim 4 to produce oxalate complexed to the Cu(II) form of the compound of claim 4;
(b) reacting the oxalate complex from step (a) with a mineral acid to liberate oxalate from the Cu(II) form of the compound of claim 4;
(c) reducing the Cu(II) form of the compound of claim 4 from step (b) to regenerate the Cu(I) form of the compound of claim 4.

* * * * *